(12) United States Patent
Ott et al.

(10) Patent No.: US 8,551,049 B2
(45) Date of Patent: *Oct. 8, 2013

(54) DEVICE AND METHOD FOR EVACUATING SURGICAL VAPOR AND MIST FROM A BODY CAVITY

(75) Inventors: Douglas E. Ott, Macon, GA (US); Nathaniel V. Tran, Apple Valley, MN (US)

(73) Assignee: Lexion Medical, LLC, St. Paul, MN (US)

( * ) Notice: Subject to any disclaimer, the term of this patent is extended or adjusted under 35 U.S.C. 154(b) by 78 days.

This patent is subject to a terminal disclaimer.

(21) Appl. No.: 13/157,434

(22) Filed: Jun. 10, 2011

(65) Prior Publication Data

US 2012/0316510 A1    Dec. 13, 2012

(51) Int. Cl.
*A61M 5/178* (2006.01)

(52) U.S. Cl.
USPC ...... 604/167.03; 604/23; 604/26; 604/167.05

(58) Field of Classification Search
USPC .............. 604/23–26, 167.03, 167.05
See application file for complete search history.

(56) References Cited

U.S. PATENT DOCUMENTS

| 5,199,944 | A | 4/1993 | Cosmescu |
| 6,592,543 | B1 | 7/2003 | Wortrich et al. |
| 7,789,946 | B2 | 9/2010 | Schultz et al. |
| 7,854,724 | B2 | 12/2010 | Stearns et al. |
| 2002/0128603 | A1 | 9/2002 | Booth et al. |
| 2010/0185139 | A1 | 7/2010 | Stearns et al. |
| 2010/0241061 | A1 | 9/2010 | Ott et al. |

*Primary Examiner* — Emily Schmidt
(74) *Attorney, Agent, or Firm* — Winthrop & Weinstine, P.A.

(57) ABSTRACT

Devices and methods for vacuum-assisted removal of surgically contaminated gas from an insufflated body cavity, the contaminants comprising smoke, aerosols, vapor, mist and the like generated during surgical procedures in order to clear the surgeon's vision of the surgical site and prevent exposure of the surgical staff to the gas. One embodiment of the present invention comprises a series of flow restriction devices to enable stepping down of the flow rate generated by an external vacuum. This reduced flow rate allows safe yet rapid removal of the toxic and vision-obstructing surgical byproducts from the patient's body cavity. The initial flow restriction device may comprise a perforated trocar sleeve in fluid communication with the vacuum source that allows retention of the surgical instrument within the trocar sleeve's inner lumen with concurrent smoke removal. A series of additional flow restriction devices located downstream of the perforated sleeve's intake ports are employed to safely limit the flow rate to a manageable and known value.

8 Claims, 7 Drawing Sheets

DEVICE AND METHOD FOR EVACUATING SURGICAL VAPOR AND MIST FROM A BODY CAVITY

BACKGROUND OF THE INVENTION

1. Field of the Invention

The invention relates to devices and methods for evacuation of contaminated gas within a surgical cavity during certain surgical procedures.

2. Description of the Related Art

During the performance of certain surgical procedures a surgeon may need to use a needle or a trocar device to deliver fluid into a body cavity, or a portion of a body, for the purposes of inflating or distending the body cavity to make it easier to see and perform the desired treatment. Common procedures in which insufflation is used include any type of an endoscopic surgical procedure, as well as laparoscopic or thoracoscopic surgical procedures performed in the abdominal or thoracic body cavities, respectively. In these procedures a blind incision, for example, or a Verres needle may be used to initially traverse the skin and tissue layers until the body cavity is entered for the purpose of passing a pressurized fluid, either a gas or a liquid, into the body cavity.

When a blind incision is made, a standard trocar assembly may then be passed through the incision and into the body cavity, whereupon the desired fluid is passed through the trocar into the body cavity. If a Verres needle has been used to penetrate the body cavity, an external gas source is attached to a proximal end of the needle projecting outwardly from the body cavity. Under pressure, the desired fluid flows through the needle and is delivered into the body cavity for inflating the body cavity. In either instance, this process is known as insufflation, in which the desired fluid, as well as any other substances, which may include drugs and anesthetics, is passed under pressure into the body cavity. A commonly used gas for this procedure is carbon dioxide. Depending on the patient's size, medical condition, the procedure to be performed, and the surgeon's preference, the gas is flowed into the body cavity at a rate of from 0.1 to 20 liters per minute.

As described, physicians may use trocar assemblies for the purposes of passing a pressurized fluid within a body cavity. Known trocar assemblies have a solid outer sheath or a sleeve that is sized and shaped to allow passage through the incision and tissue layers of a body so that the sleeve penetrates at least partially into the body cavity. This is accomplished by passing an elongate central retracting piercing element, referred to as a trocar or an obturator, through the sleeve and then passing the sleeve and the trocar together through the tissue. Once the sleeve is passed into the body cavity to the desired depth, the trocar is withdrawn from the sleeve.

During the insufflation process the pressurized fluid distends the body cavity to move the tissue layers outwardly of the body to create sufficient space in the cavity to observe and/or treat the organs and/or body structures therein. Once the body cavity is sufficiently distended and the trocar is withdrawn from the lumen of the trocar sleeve, surgical instruments are typically passed through the lumen, while fluid continues to flow. This allows the surgeon to visualize the contents of the body cavity and proceed with the desired diagnostic and/or surgical procedures without damaging the remaining tissues, organs, or body structures within the body cavity.

Use of the surgical tools to cut body tissue generates contaminants and byproducts comprising smoke, aerosols, vapor and mist, etc., that disrupts the surgeons view of the surgical site and may present health risks to the surgical staff if exposed. Past attempts to safely and effectively remove the contaminated gas include simply releasing the smoke into the surgical environment, exposing the surgical team to the smoke and its contaminants. Other solutions comprise using the pressure in the surgical cavity to drive gas outflow, and filtration. This is unsatisfactory because reliance on the surgical cavity pressure may often be insufficiently effective in removing the contaminated gas as quickly as desired.

Other solutions use a vacuum source in line and in fluid communication with the surgical cavity. These solutions must be very controlled in restricting the fluid flow rate so as to permit a rapid gas/smoke removal while reinsufflating the surgical cavity to compensate for the gas/smoke that is removed in order to maintain sufficient pressure and distension within the surgical cavity. The abdominal cavity of the average patient comprises approximately two liters in volume, thus, a relatively low flow rate is required in order to remove smoke from the cavity. The smoke removal procedure may require a relatively rapid and full gas exchange within the surgical cavity in order to remove the smoke. Such gas/smoke removal should be done as quickly as possible in order to allow the surgeon vision of the site and to expedite the surgical procedure. A typical wall vacuum comprises relatively high flow rates, which requires that flow restrictions be placed along the fluid conduit in order to bring the flow rate in the surgical cavity to within the range of 0 to 30 liters per minute. Known solutions comprise providing a filter with sufficient resistance to reduce the flow rate of the fluid passing therethrough and/or predetermined orifice sizing combinations placed in fluid communication with the vacuum and surgical cavity. These solutions rely on manipulation of the filter composition and size and/or predetermined and fixed sized orifice combinations in order to achieve a safe flow rate.

The present invention overcomes these deficiencies.

BRIEF SUMMARY OF THE INVENTION

Devices and methods for vacuum-assisted removal of surgically contaminated gas from an insufflated body cavity, the contaminants comprising smoke, aerosols, vapor, mist and the like generated during surgical procedures in order to clear the surgeon's vision of the surgical site and prevent exposure of the surgical staff to the gas. One embodiment of the present invention comprises a series of flow restriction devices to enable stepping down of the flow rate generated by an external vacuum. This reduced flow rate allows safe yet rapid removal of the toxic and vision-obstructing surgical byproducts from the patient's body cavity. The initial flow restriction device may comprise a perforated trocar sleeve in fluid communication with the vacuum source that allows retention of the surgical instrument within the trocar sleeve's inner lumen with concurrent smoke removal. A series of additional flow restriction devices located downstream of the perforated sleeve's intake ports are employed to safely limit the flow rate to a manageable and known value.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1A:
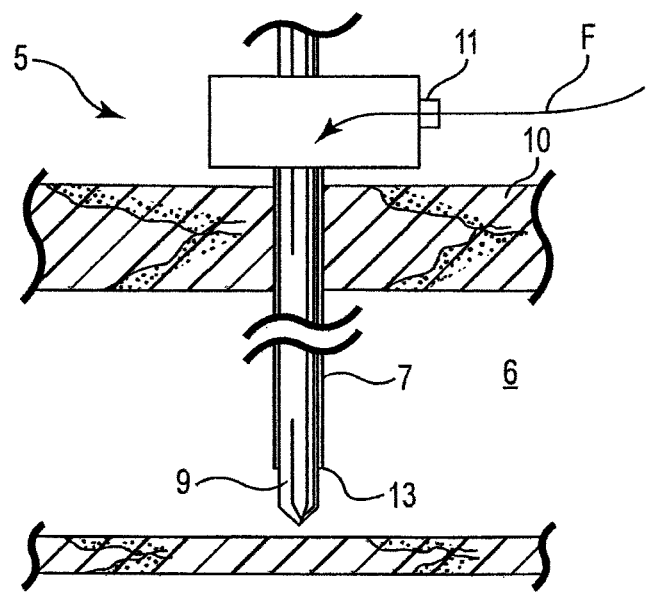
FIGS. 1A and B are partial cross-sectional illustrations of a known type of trocar sleeve.

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

An example of the known types of trocar assemblies is illustrated in FIGS. 1A and B, in which a known trocar assembly 5 is shown being used to gain access to a body cavity 6. The trocar assembly is comprised of a solid outer sheath or sleeve 7, the sleeve 7 defining a central lumen (not shown) therethrough. A trocar 9, comprising a distal piercing element, is slidably disposed within the lumen of the sleeve 7. The trocar 9 is used together with the trocar sleeve 7 to pierce the skin, the subcutaneous tissue, the fascia, the muscle, and the innermost layer of the cavity, collectively referred to as 10, to include the parietal peritoneum or the pleura, respectively, for either the abdominal or chest cavities.

Figure 1B:
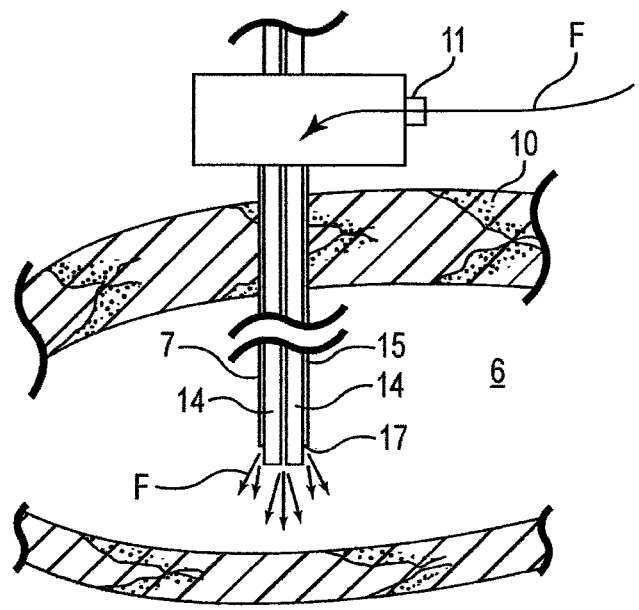

As shown in FIG. 1B, removal of the trocar 9 after accessing the body cavity 6 allows various instruments 14, to include light sources, viewing scopes, graspers, manipulators, irrigators, suction devices, sutures, lasers, coagulators, biopsy devices, clip appliers and needle holders, may be placed through the lumen of the trocar sleeve 7 and into the body cavity 6 for the treatment or procedure to be performed.

As illustrated, the trocar assembly 5 is inserted into the body cavity, a pressurized fluid "F" from an external source, which may be a gas or a liquid bearing drugs, anesthetics, or other substances placed or mixed within a pharmaceutically acceptable carrier, or any combination thereof, is commonly passed through the access port 11 and transported into the body cavity through the distal end 13 of the trocar sleeve. It is commonplace in procedures of this type that the fluid F will also continue to be passed into the body cavity once the trocar is removed. The access port 11 extends from the proximal end of the trocar sleeve 7 exposed above the skin of the patient.

Once the body cavity is sufficiently distended with pressurized fluid F, the surgeon may then view the surgical site and use lasers, ultrasonic tissue fragmentation devices and/or electrocautery devices and the like for cutting of tissues and/or blood vessels during the surgical procedure. These cutting processes produce undesirable contaminants comprising potentially contaminated smoke, aerosols, vapor, mist and other undesirable byproducts that can cloud or obstruct the surgeon's view of the operative site. The gas within the surgical cavity thus likely contains toxic and unpleasant substances that could expose the surgical staff to a health risk and disrupts the surgeon's view of the surgical site; therefore, the contaminated gas must be safely and efficiently removed from the surgical cavity.

Because, as illustrated in FIG. 1B, the known trocar sleeve 7 will typically have at least one surgical instrument and/or a viewing device placed within its lumen throughout the surgical procedure, the cross-sectional area 15 of the unobstructed lumen available for removal outflow of the smoke, is markedly reduced. The contaminated evacuated gas, i.e., smoke is forced to flow out of the cavity through a relatively small opening 17 in the distal end of the trocar sleeve, then between the outer surface of the instrument(s) within the lumen and the internal surface of the trocar sleeve, which restricts the amount of contaminated fluid, i.e., smoke that may be passed through the trocar sleeve.

Figure 2:
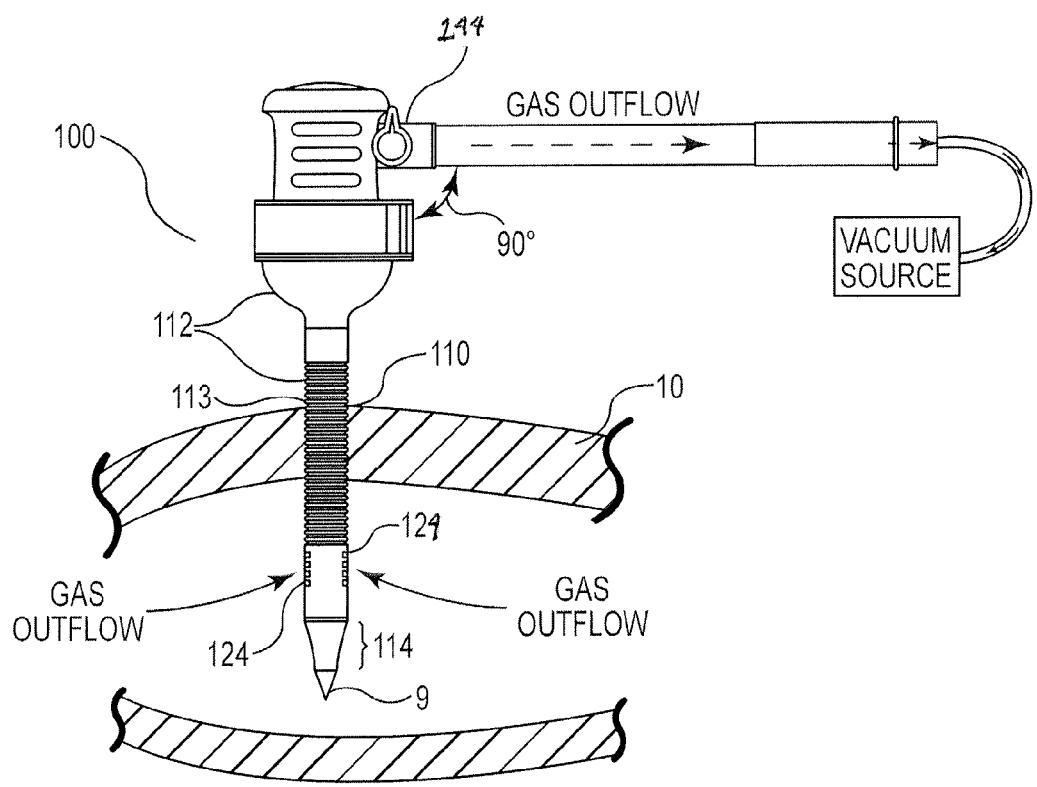
FIG. 2 is a side view of one embodiment of the present invention.
Figure 3:
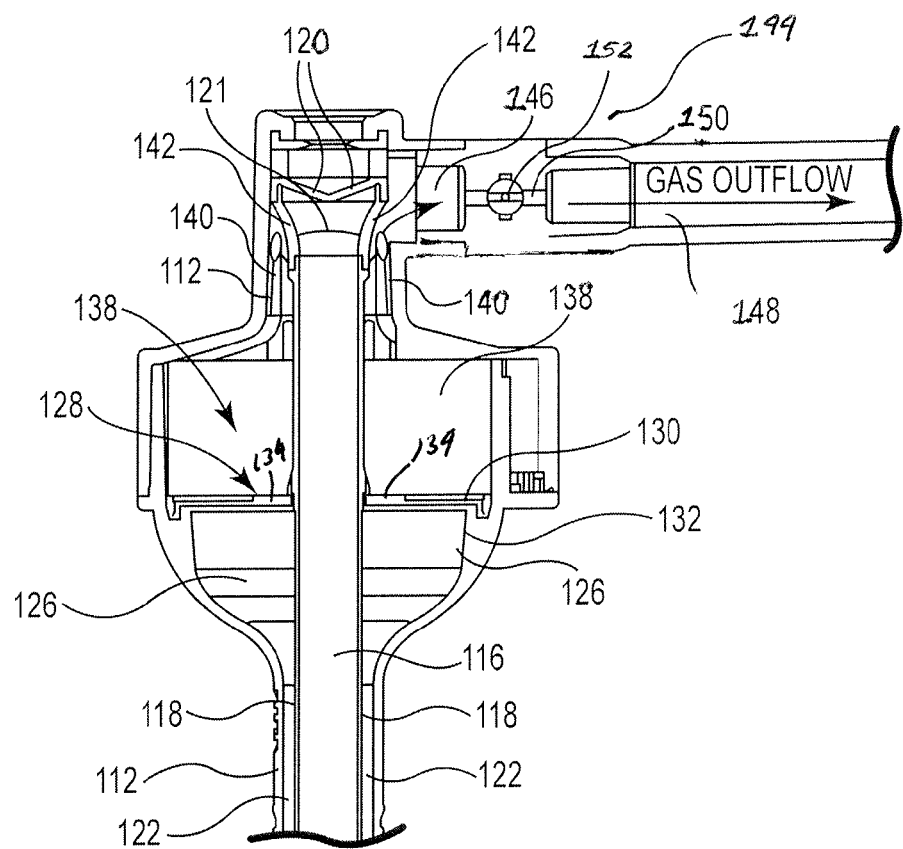
FIG. 3 is a cross section of one embodiment of the present invention.
Figure 3:
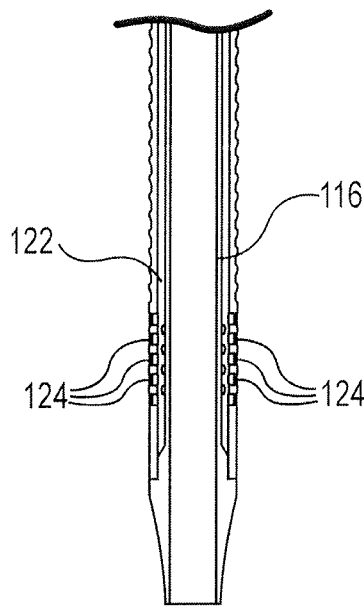

FIGS. 2 and 3 illustrate one embodiment of a dual lumen gas evacuation device 100 of the present invention inserted through the skin, the subcutaneous tissue, the fascia, the muscle, and the innermost layer of the cavity 10 as described supra. Generally, an elongate trocar sleeve 110 is defined by a housing wall 112 which may be formed of a rigid or resilient plastic, from a metal, or of any desired material suitable for use as a trocar sleeve 110. In general, what is required is that the housing and other elements of the various embodiments of the present invention be constructed of material approved by the United States Food and Drug Administration for use in surgical procedures, that the material(s) be durable, and capable of being completely sterilized for subsequent re-use. It is also anticipated that the inventive device may be constructed as a disposable single-use device, i.e., without need for resterilization and re-use. Ridges 113 are formed along at least a portion of the sleeve 110 in order to assist in stabilization of the sleeve 110 when positioned.

The trocar sleeve 110 further comprises a distal tapered section 114 to assist with ease of access through the tissue 10 and entry to the body cavity 6. An inner-most lumen or working channel 116 is defined by a working channel wall 118 disposed within the trocar sleeve 110 and provides a working channel 111 comprising access to the surgical or body cavity 6 through which the surgeon may introduce instruments for communication within the surgical cavity 6. In addition, the working channel 116 slidingly receives a trocar 9, as illustrated in FIG. 2 and which is similar to that illustrated in FIG. 1A, wherein the trocar tip 9 is extending distally beyond the distal end of the trocar sleeve 110. The preferred working channel lumen 116 may be sized to admit a 5 mm diameter instrument, though additional embodiments comprise a working channel lumen 116 that can accommodate instruments therein that range from 3 mm to 14 mm in diameter. As those skilled in the art will readily recognize, the trocar sleeve 100, and the working channel 116, may also be adapted in length to accommodate certain procedures. For example, bariatric laparoscopic procedures may benefit from a longer trocar sleeve 110 and working channel 116 according to the present invention's various embodiments. However, it is important to understand that the size and shape of the present invention is not limited to laparoscopy, e.g., and may, therefore, be adapted and used in other procedures in various embodiments of the present invention.

At least two valves 120, 121, may be in operative communication with the working channel 116 to allow access to the surgical cavity 6 while restricting outflow of the contaminated surgically generated gas to the extent possible through the working channel 116. In the illustrated embodiment the duckbill valve 120, prevents evacuation of contaminated gases from the body cavity when an instrument is absent from the working channel 116. The tool seal valve 121, as illustrated a self-sealing elastomeric valve as is known in the art, prevents evacuation of contaminated gases from the body cavity when an instrument is inserted in the working channel 116. Other types of valves 120, 121 are known in the art; each of these valve types are within the scope of the present invention.

An outer secondary lumen 122, located and defined by the space between the working channel wall 118 and the trocar sleeve housing 112, comprises a secondary lumen through which gas is evacuated from the surgical cavity 6 through a plurality of gas evacuation ports 124 located on and through the trocar sleeve housing 112, the gas evacuation port holes 124 extending through the sleeve housing 112 and, therefore, being in fluid communication with the secondary lumen 122. The gas flows into the gas evacuation ports 124 as illustrated in FIG. 2 and upward through the secondary lumen 122 in response to an external vacuum source, located downstream, and that is in operative and fluid communication with the secondary lumen 122, the gas evacuation ports 124 and the surgical/body cavity 6.

Figure 4:
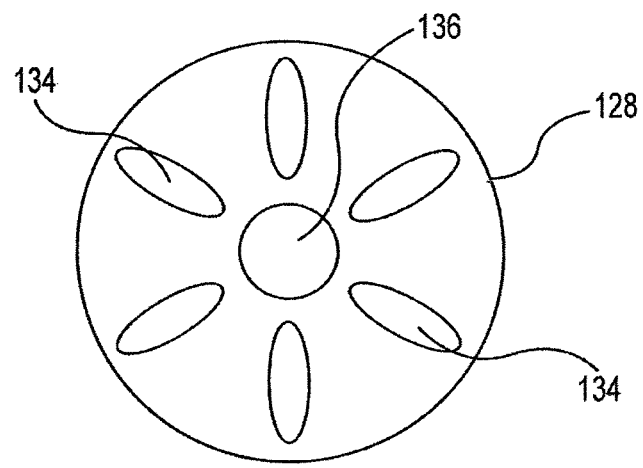
FIG. 4 is a bottom view of one embodiment of a restrictor plate of the present invention.

The housing 112 expands proximally in volume to define the upper chamber 126 which is bounded by a restrictor plate 128 having a top surface 130 and a bottom surface 132 with a plurality of restrictor plate flow ports 134 therethrough to allow the evacuating gas to continue to flow upward, but at a reduced flow rate as is best illustrated in FIG. 4. Further, the restrictor plate 128 comprises a substantially central access port 136 for passage of the working channel 116. The skilled artisan will readily recognize equivalents to the illustrated flow port 134 numbers, size and shape, each of these equivalents are within the scope of the present invention.

A filtration element 138 comprising a material well known to the skilled artisan that assists in removing contaminants from the evacuating gas and also serves as a restrictive device to reduce the flow rate of the evacuating gas. In one embodiment, the filtration element 138 comprises smoke filtering charcoal elements. The pressure drop across the filtration element may be tuned in order to change the balance between contaminant filtration and gas evacuation flow rates. In another embodiment, the filtration element 138 may also comprise an anti-microbial and/or anti-bacterial layer or, alternatively, such materials may be integrated into and throughout the filtration element 138. The levels of filtration of these additional anti-microbial and/or anti-bacterial materials may be attenuated by known techniques as the skilled artisan will readily recognize in order to produce the specifically desired flow rate at the gas evacuation ports 124 at a specific, higher, external vacuum pressure.

The evacuating gas exits the filtration element 138 and enters the upper region of the secondary lumen 140 defined by the space between the outer housing 112 and the working channel wall 118 which is in fluid communication with the upper chamber 126, the restrictor plate flow ports 134, the secondary lumen 122 and the gas evacuation ports 124. At least a portion of the working channel wall 118 within the upper region of the secondary lumen 140 comprises a radiused or curved section 142 which directs the evacuating gas radially outward toward the outer housing wall 112 within the upper region of the secondary lumen 140, thereby slowing the flow rate of the evacuating gas and generating a turbulent environment as this radially directed gas impacts the housing wall 112 within the upper region of the secondary lumen 140 and rebounds therefrom and flowing directly or indirectly into the oncoming evacuating gas that has exited from the filtration element 138. This turbulence further slows the flow rate of the evacuating gas.

The evacuating gas will eventually find an outlet from the turbulent environment in the upper region of the secondary lumen 140. A flow regulation conduit 144 is in operative and fluid connection and communication with the upper region of the secondary lumen 140, at an angled connection, the preferred connection will comprise substantially a 90 degree angled connection as illustrated, though other angled connections are within the scope of the present invention. The fluid regulation conduit 144 comprises a proximal gas outflow lumen 146 and a distal gas outflow lumen 148, each comprising a diameter and a flow regulator lumen 150 disposed between the proximal and distal gas outflow lumens 146, 148 and further comprising a diameter. The flow regulation lumen 150 diameter is smaller than both of the diameters of the proximal and distal gas outflow lumens 146, 148. The flow regulation lumen 150 is in operative and fluid communication with the proximal and distal outflow lumens 146, 148.

Figure 5:
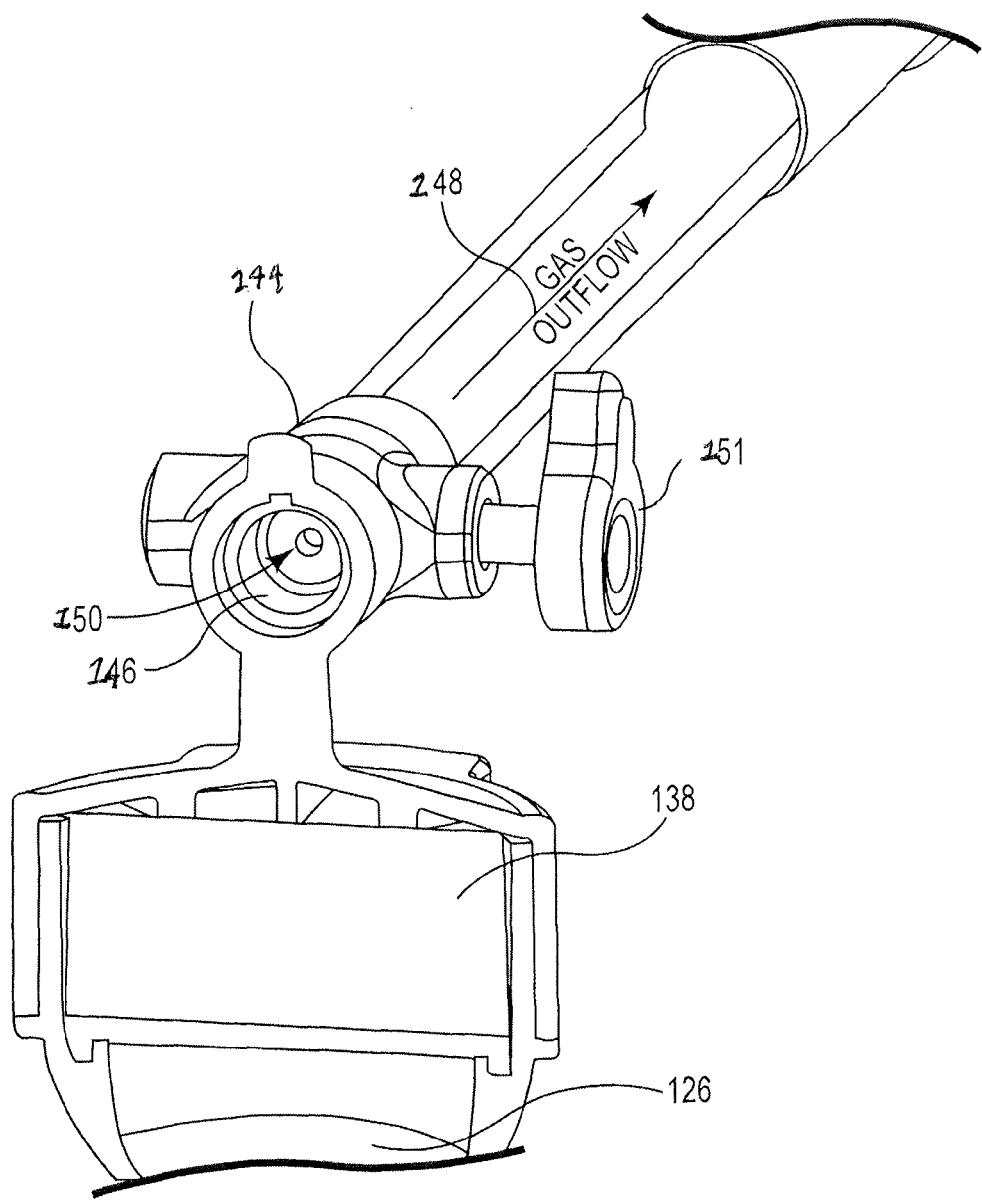
FIG. 5 is a partial cross-sectional view of one embodiment of the present invention.

The fluid regulation conduit is further illustrated in a partial cross-section and broken away view in FIG. 5, wherein the proximal gas outflow lumen 146 and the flow regulator lumen 150 are shown in relation to the cross-sectional illustration the filtration element 138 and the upper chamber 126. The working channel 116 and the upper region of the secondary lumen 140 are not shown in FIG. 5 to better illustrate the relationship between the proximal gas outflow lumen 146 and the flow regulator lumen 150. Thus, the proximal gas outflow lumen 146 is shown broken away from the point of operative and fluid communication and connection with the upper region of the secondary lumen 140 described supra.

Disposed within the flow regulator lumen 150 is a flow regulator 152 that may be actuated to allow fluid communication with the gas evacuation ports 124 and surgical cavity 6 and a downstream external vacuum and to allow fluid communication through the system to the gas evacuation ports 124 and the surgical cavity 6 as described herein. The flow regulator 152 may be a stopcock as is well known in the art, wherein the fluid flow is either fully "ON" or fully "OFF" and actuated by simply turning the flow regulator 152 to align an orifice therethrough with the flow regulator lumen 150 or turning the flow regulator 152 to eliminate alignment thereof. In other embodiments, the flow regulator 152 may comprise a series of variably sized orifices axially spaced along the length of the flow regulator 152 which are well known in the art and that may be actuated by aligning the desired orifice with the flow regulator lumen 150 in a known manner. The distal gas outflow lumen 148 is in operative and fluid communication with an external vacuum source that provides the motive force for the gas evacuation flow through the entire system.

Thus, the dual lumen embodiment provides a fluid conduit that provides a pathway for the evacuating gas from the bodily cavity to a container (not shown) for proper disposal, driven by vacuum pressure provided by an external vacuum source in fluid communication and operative connection with the fluid conduit while allowing the surgeon full access to the surgical cavity 6 through the working channel 116. The structures along the fluid conduit are designed to provide an overall flow rate reduction at the gas evacuation ports 124 and within the surgical cavity 6, necessary to prevent unwanted and potentially damaging effects that may be induced by the relatively high pressure of the external vacuum source as discussed infra.

The fluid conduit begins at the gas evacuation ports where the contaminated gas enters the trocar sleeve 110 at the plurality of gas evacuation ports 124 shown as disposed generally on the distal end of the elongate trocar sleeve 124 in response to a vacuum pressure applied at the downstream end of the fluid conduit. The gas evacuation ports 124 may be distributed at other locations along the elongate trocar sleeve 110 and, therefore, are not restricted to the distal end of the trocar sleeve 110, but rather must be disposed within the surgical cavity 6.

After the trocar sleeve 110 is positioned within a surgical cavity 6 and the surgeon determines the necessity of clearing the surgical cavity of mist, vapor, smoke and other contaminants generated during cutting and the like, the fluid conduit may be actuated by moving the flow regulator to an "ON" position and starting or turning on the in-line vacuum source to cause a vacuum airflow through the fluid conduit by actuating the flow regulator 152.

First, in response to the vacuum pressure, the evacuating gas is urged into the plurality of gas evacuation ports 124 and into the secondary lumen 116. The secondary lumen 116 comprises a lower region of substantially constant diameter and volume, wherein the gas is urged under pressure upward through the constant diameter region until reaching the enlarged upper chamber 126, comprising a cross-sectional volume that is larger than any given cross sectional volume of the secondary lumen 116, creating a pressure drop and concurrent decrease in flow rate. The upper chamber 126 is bounded proximally by the restrictor plate 128 comprising a substantially central through-hole or aperture 136 for the working channel to pass through and a plurality, or at least one, restrictor plate flow ports 134, through which the evacuating gas flows.

As the evacuating gas is urged via the external vacuum source further downstream within the fluid conduit, passing through the restrictor plate flow port(s) 134, it encounters the gas filtration element 138. After exiting the gas filtration element 138, the evacuating gas enters the upper region of the secondary lumen 140 and ultimately generating a turbulent environment as the gas encounters the curved region of the working channel wall 142 and is radially urged against the housing wall of the upper region of the secondary lumen 140, rebounding from that impact only to encounter incoming evacuating gas exiting from the filtration element 138. Ultimately, the gas finds a release from this turbulent environment through the fluid regulation conduit 144 which is in operative and fluid communication and connection with one radial region of the upper region of the secondary lumen 140. As can be seen in FIG. 3, some of the evacuating gas that encounters the working channel's curved surface will be urged radially into the fluid regulation conduit 144, thereby escaping the turbulent environment.

The vacuum pressure thus ultimately urges the outflowing contaminated gas to make an angled turn into the flow regulation conduit 144, entering the proximal gas outflow lumen 146 which may comprise a smaller volume than the upper region of the secondary lumen 140. The contaminated gas then flows through the reduced diameter flow regulation lumen 150, encountering the flow regulation lumen 150 and, if present, any reduced diameter orifices which may serve to slow the volume of gas flowing therethrough. Once through the flow regulation lumen 150, the contaminated gas then enters the distal gas outflow lumen 148 comprising a diameter larger than the diameter of the flow regulation lumen 150. Ultimately, the contaminated gas may be evacuated to a waste reservoir or otherwise disposed of.

As described, there are a series of rate and/or volume flow restriction elements in the duel lumen flow conduit embodiment of the present invention, each of which contributes reduction of flow rate from the external vacuum flow rate down to the desired range of 0 to 30 liters per minute within the body cavity at the plurality of gas evacuation ports. These flow restriction elements include, but are not limited to:

1. The plurality of gas evacuation ports 124 are sized to restrict the external vacuum flow rate and volume of evacuating gas. The gas flow volume through the evacuation ports 124 is affected by the size of the ports 124 as follows: the smaller the relative size of the ports, the lower the volume therethrough which, in combination with the downstream flow restriction elements, works to reduce the flow rate and/or volume of the gas evacuating from the surgical cavity 6.

2. The volume of the secondary lumen 122, specifically the lower region of substantially constant diameter and volume, defined as the space between the walls of the trocar housing 112 and working channel 116, combined with the additional flow restriction elements may be sized to modify the flow rate and/or volume of the gas evacuating from the surgical cavity 6.

3. The diameter and volume of the upper chamber 126 which is substantially larger than that of the lower region of the secondary lumen 122, creating a pressure drop and thereby slowing the velocity of the contaminated gas flowing therethrough and, in combination with the additional flow restriction elements of the present invention may serve to reduce the flow rate and/or volume of the gas evacuating from the surgical cavity 6.

4. The size and number of the restrictor plate flow ports 134 serve to reduce the rate of flow of the contaminated gas through the fluid conduit and in combination with the additional flow restriction elements of the present invention may serve to reduce the flow rate and/or volume of the gas evacuating from the surgical cavity 6.

5. The gas filtration element 138 comprises a material which is relatively resistant to the contaminated gas flow, stripping the gas of some if not all contaminants in the process and, in combination with the additional flow restriction elements of the present invention, and may serve to reduce the flow rate and/or volume of the gas evacuating from the surgical cavity 6.

6. The turbulence created as the gas encounters the curved region of the working channel wall 142 and is radially urged against the housing wall of the upper region of the secondary lumen 112, rebounding from that impact only to encounter incoming evacuating gas exiting from the filtration element 138 and may serve, in combination with the additional flow restriction elements of the present invention, to reduce the flow rate and/or volume of the gas evacuating from the surgical cavity 6.

7. The directional change of the contaminated gas flow in flowing from the upper region of the secondary lumen 142 to the flow control conduit 144, at a preferred approximately or substantially 90 degree angle, in combination with the additional flow restriction elements of the present invention, may serve to reduce the flow rate and/or volume of the gas evacuating from the surgical cavity 6. An obtuse directional change, i.e., greater than 90 degrees affects the gas flow rate as follows: the larger the directional change angle above 90 degrees, the faster the gas flow rate at the gas evacuation ports 124, relative to a 90 degree angled connection. An acute directional change, i.e., less than 90 degrees, affects the gas flow rate at the gas evacuation ports 124 as follows: the smaller the directional change angle below 90 degrees, the slower the gas flow rate at the gas evacuation ports 124 relative to a 90 degree angled connection.

8. The smaller diameter of the flow regulator lumen 152 is then encountered, which may also limit the volume of the gas flow therethrough which, in turn and in combination with the additional flow restriction elements of the present invention, may serve to reduce the flow rate and/or volume of the gas evacuating from the surgical cavity 6.

9. When present, a reduced diameter orifice, i.e., smaller than the diameter of the flow regulator lumen 152, of the flow regulator 150, in combination with the additional flow restriction elements of the present invention, may serve to reduce the flow rate and/or volume of the gas evacuating from the surgical cavity 6.

10. Entry of the contaminated gas from the small diameter flow regulation lumen 150 into the larger diameter, and larger volume, distal gas outflow lumen 148, creating a pressure drop in the system, in combination with the additional flow restriction elements of the present invention, may serve to reduce the flow rate and/or volume of the gas evacuating from the surgical cavity 6.

The combined effect of the described flow restriction elements of the present invention are to reduce the relatively high external vacuum flow rate, for example and without limitation 40 to 100 liters per minute, to a safe, effective and efficient flow rate of 6 to 30 liters per minute at the gas evacuation ports 124. As the skilled artisan will recognize, these flow restriction elements within the inventive system may be individually modified or attenuated to bring the system into compliance with the desired flow rate at the gas evacuation ports 124, i.e., within the preferred range of flow of between 0 to 30 liters per minute. The individual flow restriction elements work in harmony with each other to provide a systematic approach to the flow rate at the gas evacuation ports 124 and within the surgical cavity 6. Attenuation of the system however, is more controllable and predictable than simply targeting a flow between 0 to 30 liters per minute at the gas evacuation ports 124. As the skilled artisan will recognize, a much tighter, more controlled, range of flow, e.g., 6 to 10 liters per minute or 25 to 30 liters per minute or any range of flow therebetween, is obtained through manipulation of the individual flow restriction elements, the actual targeted flow rate will depend on the desired evacuation time and flow.

Figure 6:
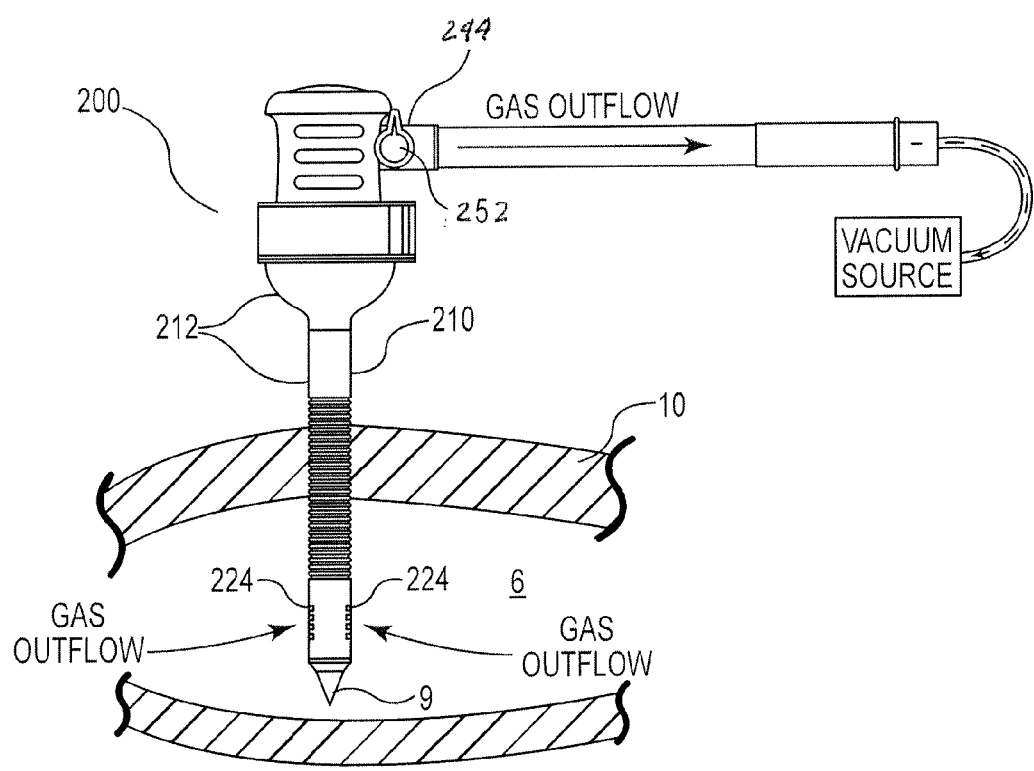
FIG. 6 is a side view of one embodiment of the present invention.
Figure 7:
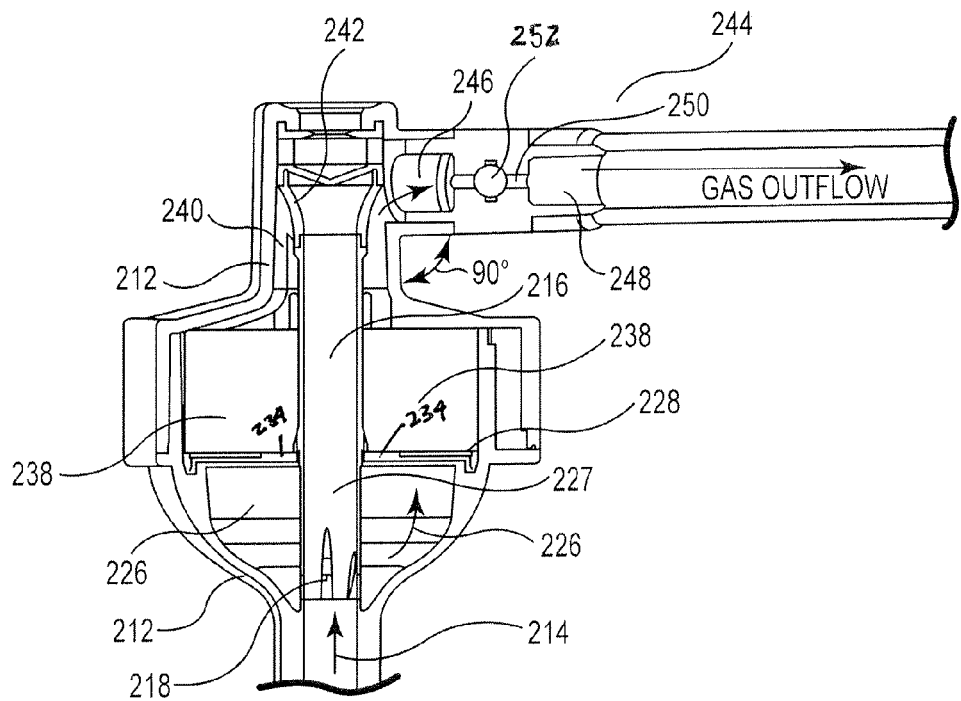
FIG. 7 is a side cross sectional and cutaway view of one embodiment of the present invention.
Figure 8:
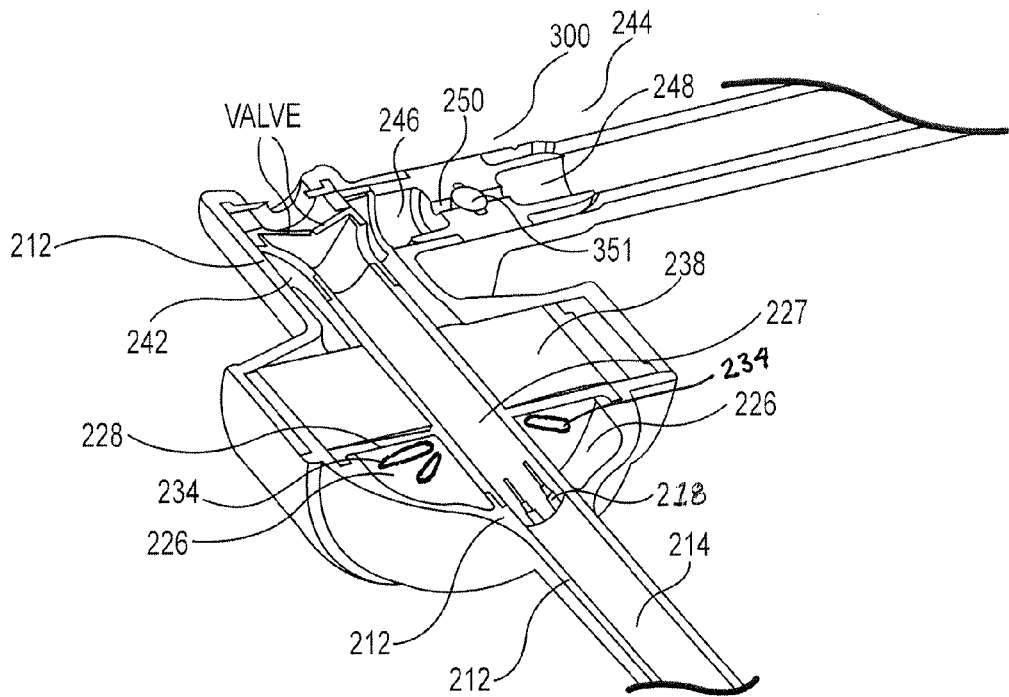
FIG. 8 is a perspective cross sectional and cutaway view of one embodiment of the present invention.

FIGS. 6-8 illustrate another embodiment of the present invention comprising a single lumen trocar 200 with a gas evacuating conduit for contaminated gas evacuation. A distal portion of the evacuating gas conduit also serves a dual purpose as a working channel for instrument manipulation. One advantage of this configuration and embodiment is that a smaller diameter device than the dual lumen device 100 may be introduced into the patient, since there is no requirement for an outer secondary lumen 122 surrounding the working channel 116 as in the dual lumen embodiment discussed herein, thereby potentially reducing trauma.

The preferred single lumen in this alternate embodiment is sized to admit a 5 mm diameter instrument, though additional embodiments comprise a single lumen that can accommodate instruments therein that range from 3 mm to 14 mm in diameter, but this embodiment allows a space around the instrument within the single lumen for evacuation of contaminated gas. As those skilled in the art will readily recognize and as discussed supra, an elongate trocar sleeve 210 and the single lumen 214, both defined by housing 212, may also be adapted in length to accommodate certain procedures. For example, bariatric laparoscopic procedures may benefit from a longer trocar sleeve 210 and single lumen 214 according to the present invention's various embodiments. However, it is important to understand that the size and shape of the present invention is not limited to laparoscopy, e.g., and may, therefore, be adapted and used in other procedures in various embodiments of the present invention.

As shown in FIG. 7, this alternate embodiment comprises an evacuating gas conduit comprising a lumen having a lower portion 214 that serves dual functions as a working channel allowing instrument access as well as contaminated gas evacuation in response to a downstream vacuum source and an upper portion 216 that serves only working channel instrument access functions.

As the vacuum source is activated and the flow regulator 252 is actuated, contaminated gas will begin traveling through the plurality of gas evacuation ports 224 which are disposed through the housing wall 212, allowing fluid communication between the lower portion of the single lumen 214 and the surgical cavity 6. As the evacuating gas enters the gas evacuation ports 224, it is then urged via vacuum pressure upward through the evacuating gas conduit. When the evacuating gas reaches the entry to the upper chamber 226, the structure and function of which is the same as that element 126 is discussed supra, it encounters a plurality of apertures 218 that provide fluid communication with the lower portion of the single lumen 214, the gas evacuation ports 224, the surgical cavity 6 and the upper chamber 226. Since the upper chamber 226 is also in fluid communication with the external vacuum source, the evacuating gas is urged through the ports 228 from the lower portion of the single lumen 214 and into the upper chamber 226. It is at this point in this embodiment that two separate lumens exist, the upper portion of the single lumen 216, i.e., that portion of the single lumen disposed above the apertures 218 and that serves only the function and purpose of a working channel for allowing instrument access to the surgical site 6 therethrough, and the evacuating gas conduit. The lower portion of the single lumen 214, i.e., that portion of the single lumen below the apertures 218, performs both working channel for instrument access functions as well as gas evacuation functions; these functions are bifurcated at the apertures 218. Therefore, to this point the evacuating gas conduit comprises the plurality of gas evacuation ports 224 disposed in the lower portion of the single lumen, the lower portion of the single lumen 214, the plurality of apertures 218 that allow fluid communication with the lower portion of the single lumen 214 and the upper chamber 226, and the upper chamber 226.

In this embodiment, the trocar sleeve housing expands in volume to define the upper chamber which is bounded by a restrictor plate 228 having a top surface and a bottom surface with a plurality of restrictor plate flow ports 234 therethrough to allow the evacuating gas to continue to flow upward, but at a reduced flow rate. Restrictor plate 228 comprises the same structure and functions in this embodiment 200 as element 128 discussed supra. The restrictor plate 228 may be formed integral to the housing of the trocar sleeve. One embodiment of the restrictor plate is illustrated in FIG. 4. The skilled artisan will readily recognize equivalents to the flow port number, size and shape, each of these equivalents are within the scope of the present invention. The evacuating gas conduit further comprises the restrictor plate flow ports 234.

A filtration element 238 having a height and comprising a material well known to the skilled artisan that assists in removing contaminants from the evacuating gas and also serves as a restrictive device to reduce the flow rate of the evacuating gas. In one embodiment, the filtration element 238 comprises smoke filtering charcoal elements. The pressure drop across the filtration element 238 may be tuned in order to change the balance between contaminant filtration and gas evacuation flow rates. In another embodiment, the filtration element 238 may also comprise an anti-microbial and/or anti-bacterial layer or, alternatively, such materials may be integrated into and throughout the filtration element. The levels of filtration of these additional anti-microbial and/or anti-bacterial materials may be attenuated in order to produce the specifically desired flow rate at a specific external vacuum pressure. The evacuating gas conduit thus further comprises the filtration element 238.

The evacuating gas exits the filtration element 238 and enters the upper region of the evacuating gas conduit 240. The upper portion of the single lumen 216 comprises a radiused or curved section 242 which directs the evacuating gas radially outward toward the trocar housing 212, thereby slowing the flow rate of the evacuating gas and generating a turbulent environment as this radially directed gas impacts the housing wall 212 and rebounds therefrom and flowing directly or indirectly into the oncoming evacuating gas that has exited from the filtration element. This turbulence further slows the flow rate of the evacuating gas. The evacuating gas conduit thus further comprises the upper region of the evacuating gas conduit 240.

The evacuating gas will eventually find an outlet from the turbulent environment in the upper region of the evacuating gas conduit 240. A flow regulation conduit 244 is in operative and fluid connection and communication with the upper region of the evacuating gas conduit 240, at an angled connection, the preferred connection will comprise substantially a right angle as illustrated, though other angled connections are within the scope of the present invention. The fluid regulation conduit 244 comprises a proximal gas outflow lumen 246 and a distal gas outflow lumen 248, each of which comprise a diameter, and a flow regulator lumen 250, which also comprises a diameter. The flow regulation lumen 250 diameter is generally smaller than both of the diameters of the proximal and distal gas outflow lumens 246, 248. The flow regulation lumen 250 is in operative and fluid communication with the proximal and distal outflow lumens 246, 248, each of which comprises a diameter larger than the diameter of the flow regulation lumen 250. The evacuating gas conduit further comprises the flow regulation conduit 144 and the elements comprising the flow regulation conduit.

Disposed within the flow regulator lumen 250 is a flow regulator 252 that may be actuated to allow fluid communication with the gas evacuation ports 224 and a downstream external vacuum and to allow fluid communication through the system to the gas evacuation flow ports 224 and the surgical cavity 6. The flow regulator 252 may be a stopcock as is well known in the art, wherein the fluid flow is either fully "ON" or fully "OFF". In other embodiments, the flow regulator 252 may comprise a series of variably sized orifices which are well known in the art and that may be actuated in line with the flow regulator lumen in a known manner and which are described supra as element 152. Alternatively, the flow regulator 252 may be rotated to align an orifice with the flow regulator lumen to actuate or rotationally eliminate alignment the orifice with the flow regulator lumen 250 to deactivate. The evacuating gas conduit further comprises the flow regulator 252.

Thus, the single lumen embodiment illustrated in FIGS. 6-8 provide an evacuating gas conduit that provides a pathway for the evacuating gas from the bodily cavity to a container (not shown) for proper disposal, driven by vacuum pressure provided by an external vacuum source in fluid communication and operative connection with the evacuating gas conduit. The structures along the evacuating gas conduit provide for an overall flow rate reduction at the gas evacuation ports and within the surgical cavity, necessary to prevent unwanted and potentially damaging effects that may be induced by the relatively high pressure of the external vacuum source as discussed infra.

The evacuating gas conduit begins at the gas evacuation ports 224 where the contaminated gas enters the trocar sleeve 210 at the plurality of gas evacuation ports 224 shown as disposed generally on the distal end of the lower portion of the single lumen 214 in response to a vacuum pressure applied at the downstream end of the gas evacuating gas conduit. The gas evacuation ports 224 may be distributed at other locations along the elongate trocar sleeve 210 and, therefore, are not restricted to the distal end of the lower portion of the single lumen 214

After the trocar sleeve 214 is positioned within a surgical cavity 6 and the surgeon determines the necessity of clearing the surgical cavity of contaminants generated during cutting and the like, the gas evacuating conduit may be actuated by moving the flow regulator 252 to an "ON" position and starting or turning on the external vacuum to cause a vacuum airflow through the evacuating gas conduit.

First, in response to the vacuum pressure, the evacuating gas is urged into the plurality of gas evacuation ports 224 and into the lower portion of the single lumen 214 which comprises substantially constant diameter and volume, wherein the gas is urged upward through the constant diameter region until reaching the plurality of apertures 218 disposed between the upper chamber 226 and the lower portion of the single lumen 214, allowing fluid communication therebetween. The upper chamber 226 comprises a volume that is larger than the volume of the lower portion of the single lumen 214, particularly when an instrument is disposed therein. The enlarged upper chamber 226 comprises the restrictor plate 228 comprising a central through-hole or aperture 227 for the working channel to pass through and a plurality, or at least one, restrictor plate flow ports 234.

As the evacuating gas is urged via the external vacuum source further downstream within the evacuating gas conduit, passing through the restrictor plate flow port(s) 234, it encounters a gas filtration element 238 which further impedes the contaminated gas flowing therethrough. After exiting the gas filtration element 238, the evacuating gas enters the upper region of the evacuating gas conduit 240 and ultimately generating a turbulent environment as the gas encounters the upper portion of the single lumen 216, in particular the radiused or curved section 242, and is radially urged against the trocar housing wall 212, rebounding from that impact only to encounter incoming evacuating gas exiting from the filtration element 238. Ultimately, the gas finds a release from this turbulent environment through the fluid regulation conduit 244 which is in operative and fluid communication and connection with one radial region of the upper region of the secondary lumen 240. As can be seen in FIG. 8, as well as the embodiment of FIG. 3 which shares this structural feature, some of the evacuating gas that encounters the curved surface of the upper portion of the single lumen 242 will be urged radially into the fluid regulation conduit 244, thereby escaping the turbulent environment.

The vacuum pressure then urges the outflowing contaminated gas to make an angled turn, preferably a 90 degree angled turn, though other angles are within the scope of the present invention, into the flow regulation conduit 244, entering the proximal gas outflow lumen 246 which comprises a smaller volume than the upper region of the secondary lumen 240, thereby restricting the volume of gas flowing through the proximal gas outflow lumen 246. The contaminated gas then flows through the reduced diameter flow regulator lumen 250, encountering the flow regulator 250 and, if present, any reduced diameter orifices which may serve to slow the volume of gas flowing therethrough. Once through the flow regulator lumen 250, the contaminated gas then enters the distal gas outflow lumen 248 which comprises a diameter larger than the diameter of the flow regulation lumen 250. Ultimately, the contaminated gas is evacuated to a waste reservoir.

As described, there are a series of rate and/or volume flow restriction elements in the single lumen evacuating gas conduit embodiment 200 of the present invention, each of which contributes reduction of flow rate from the external vacuum flow rate down to the desired range of 0 to 30 liters per minute within the body cavity at the plurality of gas evacuation ports 224. These flow restriction elements include:

1. The plurality of gas evacuation ports 224 which are sized to restrict the external vacuum flow rate. The gas flow volume through the gas evacuation ports 224 is affected by the size of the ports 224 as follows: the smaller the relative size of the ports, the lower the volume therethrough which, in combination with the downstream flow restriction elements, may serve, to reduce the flow rate and/or volume of the gas evacuating from the surgical cavity 6.

2. The number and size of the apertures 218 between the upper chamber 226 and the lower portion of the single lumen 214 may, in combination with the additional flow restrictions of the present invention, serve to reduce the flow rate and/or volume of the gas evacuating from the surgical cavity 6.

3. The diameter and volume of the upper chamber 226 which is substantially larger than that of the lower region of the lower portion of the single lumen 214, works to slow the velocity of the contaminated gas flowing therethrough and, in combination with the additional flow restriction elements of the present invention may serve to reduce the flow rate and/or volume of the gas evacuating from the surgical cavity 6.

4. The size and number of the restrictor plate flow ports 234 serve to reduce the rate of flow of the contaminated gas through the evacuating gas conduit and, in combination with the additional flow restriction elements of the present invention, may serve, to reduce the flow rate and/or volume of the gas evacuating from the surgical cavity 6. The gas flow rate and/or volume of the evacuating gas from the surgical cavity 6 is directly affected by the size and number of the restrictor plate flow ports 234.

5. The gas filtration element 238 comprises a material which is relatively resistant to the contaminated gas flow, stripping the gas of some if not all contaminants in the process, thereby slowing the flow rate, in combination with the additional flow restriction elements of the present invention, may serve to reduce the flow rate and/or volume of the gas evacuating from the surgical cavity 6.

6. The turbulent environment created within the upper region of the evacuating gas conduit 240, in combination with the additional flow restriction elements of the present invention, may serve to reduce the flow rate and/or volume of the gas evacuating from the surgical cavity 6.

7. The directional change of the contaminated gas flow between the upper region of the evacuating gas conduit 240 and the flow regulator conduit 244, at a preferred approximately or substantially 90 degree angle may, in combination with the additional flow restriction elements of the present invention, serve to reduce the flow rate and/or volume of the gas evacuating from the surgical cavity 6. An obtuse directional change, i.e., greater than 90 degrees affects the gas flow rate as follows: the larger the directional change angle above 90 degrees, the faster the gas flow rate at the gas evacuation ports 224 relative to a 90 degree angled connection and directional change. An acute directional change, i.e., less than 90 degrees, affects the gas flow rate at the evacuation ports 224 as follows: the smaller the directional change angle below 90 degrees, the slower the gas flow at the gas evacuation ports 224 relative to a 90 degree angled connection and directional change.

8. The smaller diameter of the flow regulator lumen 250 is then encountered, which may also limit the volume of the gas flow therethrough which, in turn and in combination with the additional flow restriction elements of the present invention, may serve to reduce the flow rate and/or volume of the gas evacuating from the surgical cavity 6.

9. When present, the reduced diameter orifice of the flow regulator 252, when present and in combination with the additional flow restriction elements of the present invention, may also serve to reduce the flow rate and/or volume of the gas evacuating from the surgical cavity 6.

10. Entry of the contaminated gas from the small diameter flow regulation lumen 250 into the larger diameter, and larger volume, distal gas outflow lumen 248, in combination with the additional flow restriction elements of the present invention, may serve to reduce the flow rate and/or volume of the gas evacuating from the surgical cavity 6.

The combined effect of the described flow restriction elements of this embodiment 200 of the present invention are to reduce the external vacuum flow rate, and volume, to a safe, effective and efficient flow rate of 0 to 30 liters per minute at the gas evacuation ports. As the skilled artisan will recognize, these flow restriction elements may be individually modified or attenuated to bring the system into compliance with the desired flow rate at the gas evacuation ports 224, i.e., within the preferred range of flow of 0 to 30 liters per minute. The individual flow restriction elements work in harmony with each other to provide a systematic approach to the flow rate at the gas evacuation ports 224 and within the surgical cavity 6. Attenuation of the system however, is more controllable and predictable than simply targeting 0 to 30 liters per minute at the gas evacuation ports 224. As the skilled artisan will recognize, a much tighter range of flow, e.g., 6 to 10 liters per minute or 25 to 30 liters per minute or any range of flow therebetween, is obtained through manipulation of the individual flow restriction elements, the actual targeted flow rate will depend on the desired evacuation time and flow.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A device for safe, effective and efficient evacuating of contaminated insufflated gas from a surgical cavity comprising:
   a housing defining an elongate trocar sleeve having a distal tapered section;
   a working channel defined within the trocar sleeve, comprising an upper portion of a single lumen, wherein the upper portion of the single lumen functions as a working channel to allow access for instruments to the surgical cavity through the single lumen;
   a gas evacuating conduit; comprising
      a lower portion of the single lumen, the lower portion of the single lumen functioning as a working channel to allow access for instruments to the surgical cavity through the single lumen and also functioning to evacuate contaminated gas from the surgical cavity,
      a plurality of gas evacuation ports disposed through the trocar sleeve in the lower portion of the single lumen and allowing fluid communication between the surgical cavity and the lower portion of the single lumen,
an upper chamber in fluid communication with the lower portion of the single lumen, wherein the single lumen has a volume, the upper chamber having a volume that is larger than volume of the single lumen,
a plurality of apertures disposed between the upper chamber and the lower portion of the single lumen, allowing fluid communication therebetween,
a restrictor plate having an upper and lower surfaces and comprising a plurality of restrictor plate ports bounding the upper chamber, the restrictor plate ports allowing fluid communication between the upper chamber and an upper region of the gas evacuating conduit,
a filtration element disposed on the upper surface of the restrictor plate and within the upper chamber,
the upper region of a gas evacuating conduit in fluid communication with the upper chamber and defined by the trocar sleeve housing and the working channel wherein the working channel comprises a radiused curved section for directing evacuating gas radially outward against the trocar sleeve housing within the upper region of the gas evacuating conduit and creating a turbulent environment, and
a fluid regulation conduit in operative angled connection and fluid communication with the upper region of the gas evacuating conduit and the turbulent environment, comprising a proximal gas outflow lumen having a diameter, a distal gas outflow lumen having a diameter approximately the same as the diameter of the proximal gas outflow lumen, and a flow regulation lumen having a diameter that is smaller than the diameter of the proximal and distal gas outflow lumens, the flow regulation lumen further comprising a flow regulator therein for actuating the evacuating the gas from the surgical cavity; and
an external vacuum source in operative connection and actuable fluid communication with the flow regulation conduit, the upper region of the gas evacuating conduit, the filtration element, the restrictor plate ports, the upper chamber, the single lumen, the gas evacuation ports and the surgical cavity.

2. The device of claim 1, wherein the operative angled connection of the fluid regulation conduit with the upper region of the gas evacuating conduit is substantially 90 degrees.

3. The device of claim 1, wherein the operative angled connection of the fluid regulation conduit with the upper region of the region of the gas evacuating conduit comprises an acute angle.

4. The device of claim 1, wherein the operative angled connection of the fluid regulation conduit with the upper region of the region of the gas evacuating conduit comprises an obtuse angle.

5. A trocar for evacuating contaminated gas from a surgical site, comprising:
a single lumen defined within a trocar sleeve housing, comprising an upper portion of the single lumen, wherein the upper portion of the single lumen functions as a working channel to allow access for instruments to the surgical cavity through the single lumen;
a gas evacuating conduit, comprising:
a lower portion of the single lumen, the lower portion of the single lumen functioning as a working channel to allow access for instruments to the surgical cavity through the single lumen and also functioning to evacuate contaminated gas from the surgical cavity,
a plurality of gas evacuation ports disposed through a trocar sleeve in the lower portion of the single lumen and allowing fluid communication between the surgical cavity and the lower portion of the single lumen,
an upper chamber in fluid communication with the lower portion of the single lumen, the upper chamber having a volume that is larger than a volume of the single lumen,
a plurality of apertures disposed between the upper chamber and the lower portion of the single lumen, allowing fluid communication therebetween,
a restrictor plate having an upper and lower surfaces and comprising a plurality of restrictor plate ports therethrough within the upper chamber, the restrictor plate ports allowing fluid communication between the upper chamber and the upper region of the gas evacuating conduit,
a filtration element disposed on the upper surface of the restrictor plate and within the upper chamber,
the upper region of the gas evacuating conduit in fluid communication with the upper chamber and defined by the trocar sleeve housing and the working channel wherein the working channel comprises a radiused curved section for directing evacuating gas radially outward against the trocar sleeve housing within the upper region of the gas evacuating conduit and creating a turbulent environment, and
a fluid regulation conduit in operative angled connection and fluid communication with the upper region of the gas evacuating conduit and the turbulent environment, comprising a proximal gas outflow lumen having a diameter, a distal gas outflow lumen having a diameter approximately the same as the diameter of the proximal gas outflow lumen, and a flow regulation lumen having a diameter that is smaller than the diameter of the proximal and distal gas outflow lumens, the flow regulation lumen further comprising a flow regulator therein for actuating the evacuating the gas from the surgical cavity.

6. The trocar of claim 5, wherein the operative angled connection of the fluid regulation conduit with the upper region of the gas evacuating conduit is substantially 90 degrees.

7. The trocar of claim 5, wherein the operative angled connection of the fluid regulation conduit with the upper region of the gas evacuating conduit comprises an acute angle.

8. The trocar of claim 5, wherein the operative angled connection of the fluid regulation conduit with the upper region of the gas evacuating conduit comprises an obtuse angle.

* * * * *